United States Patent
Masuda

(10) Patent No.: US 12,226,204 B2
(45) Date of Patent: Feb. 18, 2025

(54) BODY MOTION DETERMINATION SYSTEM AND BIOLOGICAL STATE MONITORING SYSTEM

(71) Applicant: Minebea Mitsumi Inc., Nagano (JP)

(72) Inventor: Shigemi Masuda, Fukuroi (JP)

(73) Assignee: MINEBEA MITSUMI Inc., Nagano (JP)

( * ) Notice: Subject to any disclaimer, the term of this patent is extended or adjusted under 35 U.S.C. 154(b) by 504 days.

(21) Appl. No.: 16/636,069

(22) PCT Filed: Jul. 27, 2018

(86) PCT No.: PCT/JP2018/028208
§ 371 (c)(1),
(2) Date: Feb. 3, 2020

(87) PCT Pub. No.: WO2019/026782
PCT Pub. Date: Feb. 7, 2019

(65) Prior Publication Data
US 2021/0153777 A1 May 27, 2021

(30) Foreign Application Priority Data
Aug. 4, 2017 (JP) .................. 2017-151568

(51) Int. Cl.
*A61B 5/113* (2006.01)
*A61B 5/00* (2006.01)
(Continued)

(52) U.S. Cl.
CPC ............ *A61B 5/113* (2013.01); *A61B 5/0816* (2013.01); *A61B 5/1115* (2013.01);
(Continued)

(58) Field of Classification Search
CPC ..... A61B 5/113; A61B 5/0816; A61B 5/1115; A61B 5/4809; A61B 5/6892;
(Continued)

(56) References Cited

U.S. PATENT DOCUMENTS

2005/0080349 A1    4/2005   Okada et al.
2006/0241510 A1*   10/2006   Halperin ................ A61B 5/113
                                                                            600/534
(Continued)

FOREIGN PATENT DOCUMENTS

CN       1606962 A    4/2005
CN     104812300 A    7/2015
(Continued)

OTHER PUBLICATIONS

English-language machine translation of JP 2007-97996 (Year: 2024).*

(Continued)

*Primary Examiner* — Andrey Shostak
(74) *Attorney, Agent, or Firm* — Chrisman Gallo Tochtrop LLC

(57) ABSTRACT

A body motion determination system for determining whether a body motion of a subject (S) on a bed (BD) presents or not, includes a load detector (11, 12, 13, 14) configured to detect a load of the subject on the bed; a non-negative-valued average calculating unit (313) configured to calculate a non-negative-valued average of a detection value of the load detector; and a threshold value setting unit (315) configured to set a threshold value to be used in determining whether the body motion of the subject presents or not, based on the non-negative-valued average calculated in a resting period in which the subject merely performs a respiration.

7 Claims, 8 Drawing Sheets

(51) Int. Cl.
*A61B 5/08* (2006.01)
*A61B 5/11* (2006.01)

(52) U.S. Cl.
CPC .......... *A61B 5/4809* (2013.01); *A61B 5/6892* (2013.01); *A61B 5/7221* (2013.01); *A61B 5/7278* (2013.01); *A61B 5/7282* (2013.01); *A61B 2560/0475* (2013.01); *A61B 2562/0252* (2013.01)

(58) Field of Classification Search
CPC ... A61B 5/7221; A61B 5/7278; A61B 5/7282; A61B 2560/0475; A61B 2562/0252; A61B 5/6891; A61B 5/7228; A61B 5/1118
See application file for complete search history.

(56) References Cited

U.S. PATENT DOCUMENTS

| | | |
|---|---|---|
| 2009/0260158 A1 | 10/2009 | Kazuno et al. |
| 2010/0272294 A1* | 10/2010 | Arknaes-Pedersen ... H04R 5/04 330/69 |
| 2012/0116187 A1* | 5/2012 | Hayes .................. A61B 5/6887 600/587 |
| 2014/0088373 A1 | 3/2014 | Phillips et al. |
| 2015/0230750 A1 | 8/2015 | McDarby et al. |
| 2016/0287158 A1* | 10/2016 | Lawrenson ............ B60K 28/06 |
| 2017/0172459 A1 | 6/2017 | Berstein et al. |
| 2017/0202506 A1* | 7/2017 | Nishimura ........... A61B 5/6898 |
| 2018/0206793 A1 | 7/2018 | Akatsu et al. |
| 2020/0337634 A1 | 10/2020 | McDarby et al. |

FOREIGN PATENT DOCUMENTS

| | | |
|---|---|---|
| CN | 106974658 A | 7/2017 |
| JP | 2006-181263 A | 7/2006 |
| JP | 2007097996 A * | 4/2007 ........... A61B 5/1115 |
| JP | 4002905 B2 | 11/2007 |
| JP | 2011-104248 A | 6/2011 |
| JP | 4829020 A | 11/2011 |
| JP | 2013-198666 A | 10/2013 |
| JP | 2014-061173 A | 4/2014 |
| JP | 2014-147594 A | 8/2014 |
| JP | 2014-195543 A | 10/2014 |
| JP | 2014-233487 A | 12/2014 |
| JP | 2014-233488 A | 12/2014 |
| JP | 2014-235090 A | 12/2014 |
| JP | 2015-134032 A | 7/2015 |
| JP | 5998559 B2 | 9/2016 |
| JP | 6105703 B1 | 3/2017 |

OTHER PUBLICATIONS

International Search Report for corresponding International Application No. PCT/JP2018/028208 mailed Aug. 28, 2018.
Written Opinion for corresponding International Application No. PCT/JP2018/028208 dated Aug. 28, 2018.
Japanese Office Action dated Oct. 30, 2018 for corresponding Japanese Application No. 2017-151568 and English translation.
Japanese Office Action dated Apr. 23, 2019 for corresponding Japanese Application No. 2017-151568 and English translation.
Decision to Grant a Patent dated Jul. 30, 2019 for corresponding Japanese Application No. 2017-151568 and English translation.
Chinese Office Action dated Dec. 23, 2021 for corresponding Chinese Application No. 201880050449.5 and English translation.
Extended European Search Report dated Apr. 1, 2021 for corresponding European Application No. 18841307.4.
English translation of the Written Opinion for corresponding International Application No. PCT/JP2018/028208 dated Aug. 28, 2018.

* cited by examiner

BODY MOTION DETERMINATION SYSTEM AND BIOLOGICAL STATE MONITORING SYSTEM

TECHNICAL FIELD

The present invention relates to a body motion determination system for determining whether or not there is a body motion in a (human) subject on a bed on the basis of detection value of load detector, and a biological state monitoring system including the body motion determination system.

BACKGROUND ART

For the sites of medical treatment and caregiving service, it is proposed to determine a state of a subject on the basis of such a (body weight) load of the subject on a bed as detected by load detectors. In particular, for example, it is proposed to determine whether or not the subject has a body motion, to estimate the respiratory rate of the subject, etc., on the basis of the detected load.

Patent Literature 1 discloses a body motion level determining apparatus provided to determine a body motion level of a user on a bed in a step-up manner on the basis of detection values from load sensors arranged under the legs of the bed. Patent Literature 2 discloses a sleep determining apparatus and a turnover detecting apparatus which are capable of determining that there is a body motion in a person on a bed on the basis of detection results of a load sensor arranged under the leg of the bed.

CITATION LIST

Patent Literature 1: Japanese Patent Application Laid-open No. 2014-195543
Patent Literature 2: Japanese Patent No. 5998559, specification.

SUMMARY

Technical Problem

An object of the present invention is to provide a body motion determination system capable of determining whether or not a subject on a bed has a body motion at higher precision on the basis of detection value of load detector.

Solution to the Problem

According to a first aspect of the present invention, there is provided a body motion determination system for determining whether a body motion of a subject on a bed presents or not, the system including:
a load detector configured to detect a load of the subject on the bed;
a non-negative-valued average calculating unit configured to calculate a non-negative-valued average of a detection value of the load detector; and
a threshold value setting unit configured to set a threshold value to be used in determining whether the body motion of the subject presents or not, based on the non-negative-valued average calculated in a resting period in which the subject merely performs a respiration.

The body motion determining system according to the first aspect may further include a standard deviation calculating unit configured to calculate a standard deviation of the detection value of the load detector; and may further include a determining unit configured to determine whether the body motion of the subject presents or not based on a comparison between the calculated standard deviation and the threshold value.

The body motion determining system according to the first aspect may further include a resting period determining unit configured to determine that a period in which the standard deviation is not more than a predetermined value is the resting period. In the body motion determining system according to the first aspect, the threshold value setting unit may set the threshold value based on the non-negative-valued average calculated in the resting period determined by the resting period determining unit.

In the body motion determining system according to the first aspect, the threshold value setting unit may reset the threshold value, after the body motion determination system has determined that the body motion of the subject presents, based the non-negative-valued average calculated by the non-negative-valued average calculating unit in the resting period after the determination that the body motion of the subject presents.

According to a second aspect of the present invention, there is provided a biological state monitoring system for monitoring a biological state of a subject on a bed, the system including:
a body motion determining system according to the first aspect; and
a respiratory rate calculating unit configured to calculate a respiratory rate of the subject based on the detection value of the load detector, wherein
the respiratory rate calculating unit ceases calculating of the respiratory rate during a period for which the body motion determining system determines that the body motion of the subject presents.

The biological state monitoring system according to the second aspect may include a state determining unit configured to perform at least one of a present-in or absent-from the bed determination of the subject, an asleep or awake determination of the subject, and a dead or alive determination of the subject, based on a determination result of the body motion determination system and/or the respiratory rate of the subject calculated by the respiratory rate calculating unit.

According to a third aspect of the present invention, there is provided a bed system including:
a bed; and
the body motion determination system according to the first aspect.

According to a fourth aspect of the present invention, there is provided a bed system including:
a bed; and
the biological state monitoring system according to the second aspect.

Effect of the Invention

The body motion determination system of the present invention can determine whether or not the subject on the bed has a body motion at higher precision on the basis of the detection value of the load detector.

BRIEF DESCRIPTION OF THE DRAWINGS

FIGS. 7(a) and 7(b) are illustrative views for explaining a method for finding a non-negative-valued average over a predetermined period for such a detection value of a load detector as to vary due only to the respiration of the subject, wherein FIG. 7(a) is a graph schematically depicting an aspect of variation in the detection value before a non-negative valuing process is performed while FIG. 7(b) is a graph schematically depicting an aspect of variation in the detection value after the non-negative valuing process is performed.

DESCRIPTION OF EMBODIMENT

Embodiment

Explanations will be made on a body motion determining system according to an embodiment of the present invention, and on a biological state monitoring system 100 including the body motion determining system (FIG. 1), with an example of using the systems together with a bed BD (FIG. 2) to determine whether or not there is a body motion in a subject (human subject) S on the bed BD, and to estimate the respiratory rate of the subject S.

In the following explanation, with the center of the cuboid bed BD (FIG. 2) as the center O, the axis X of the bed BD is defined as the axis extending in the breadthwise (widthwise) direction of the bed BD and passing through the center O, and the axis Y of the bed BD is defined as the axis extending in the lengthwise (longitudinal or up/down) direction of the bed BD and passing through the center O. In planar view of the bed BD, the positive side of the axis X is the right side of the center O of the bed BD whereas the negative side of the axis X is the left side thereof, and the positive side of the axis Y is the upper side of the center O of the bed BD whereas the negative side of the axis Y is the lower side thereof. When the subject S lies on the bed BD, generally he or she lies along the axis Y and the head is placed on the positive side and the feet are placed on the negative side in the axis-Y direction.

Figure 1:
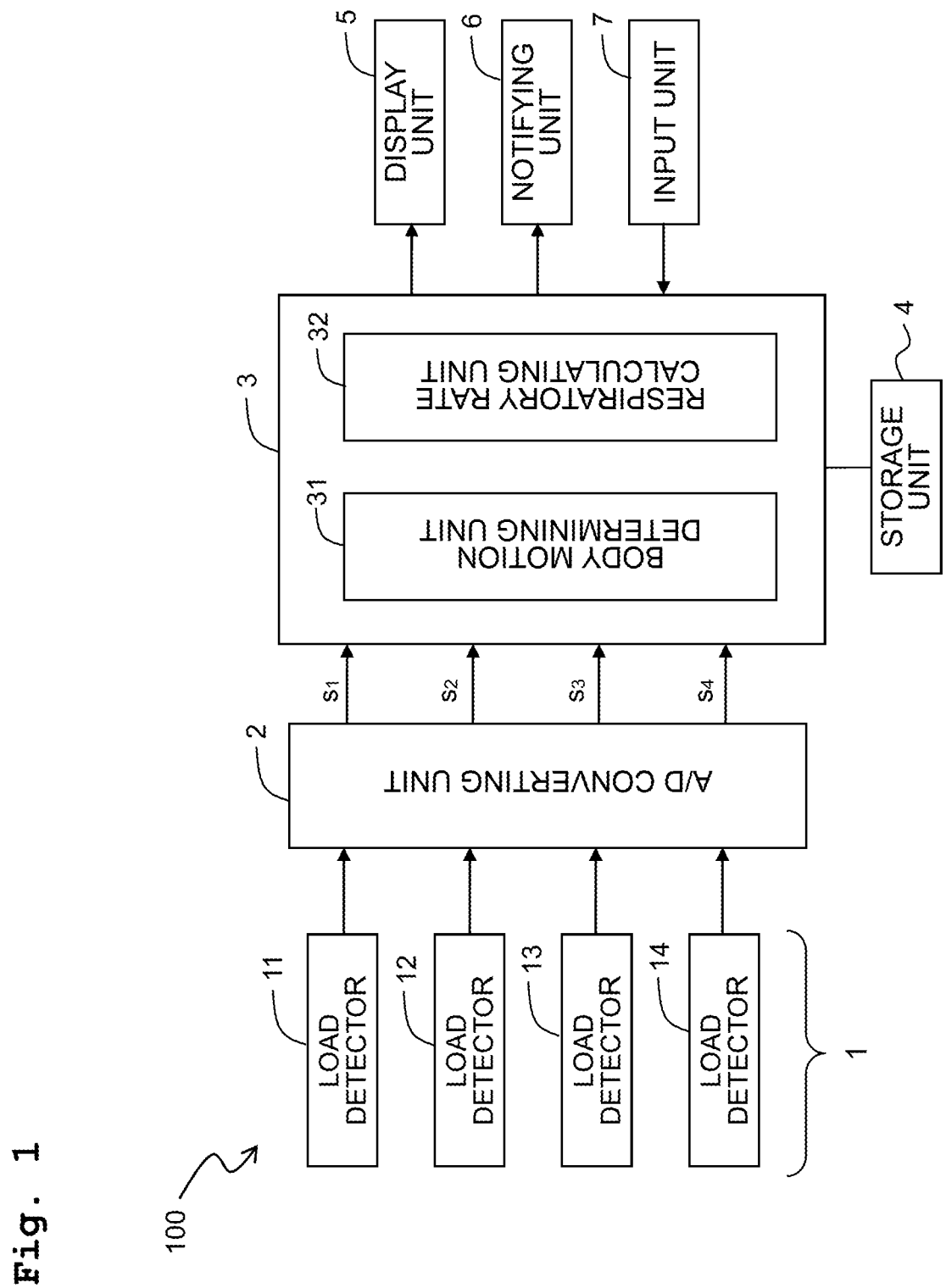
FIG. 1 is a block diagram depicting a configuration of a biological state monitoring system according to an embodiment of the present invention.

As shown in FIG. 1, the biological state monitoring system 100 of this embodiment primarily has a load detecting unit 1, a control unit 3, and a storage unit 4. The load detecting unit 1 and the control unit 3 are connected via an A/D converting unit 2. The control unit 3 is further connected to a display unit 5, a notifying unit 6, and an input unit 7.

The load detecting unit 1 includes four load detectors 11, 12, 13, and 14. Each of the load detectors 11, 12, 13, and 14 is a load detector for detecting a load by using, for example, a beam-type load cell. Such a load detector is disclosed, for example, in Japanese Patent No. 4829020 and Japanese Patent No. 4002905. Each of the load detectors 11, 12, 13, and 14 is connected to the A/D converting unit 2 by way of wiring or wirelessly.

Figure 2:
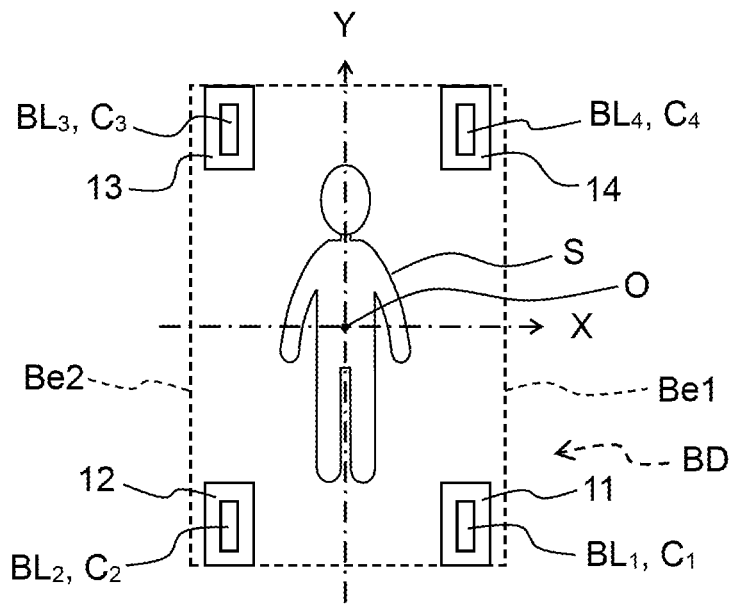
FIG. 2 is an illustrative view depicting an arrangement of load detectors for a bed.

As shown in FIG. 2, the four load detectors 11 to 14 of the load detecting unit 1 are arranged respectively under casters $C_1$, $C_2$, $C_3$, and $C_4$ fitted on the lower ends of legs $BL_1$, $BL_2$, $BL_3$, and $BL_4$ at the four corners of the bed BD used by the subject S.

The A/D converting unit 2 includes an A/D convertor connected respectively to the load detecting unit 1 and the control unit 3 by way of wiring or wirelessly, to convert analog signals from the load detecting unit 1 to digital signals.

The control unit 3 is a dedicated or general-purpose computer inside which a body motion determining unit 31 and a respiratory rate calculating unit 32 are constructed. A detailed description will be made later on about the body motion determining unit 31 determining whether or not there is a body motion in the subject S and the respiratory rate calculating unit 32 calculating (estimating) the respiratory rate of the subject S.

The storage unit 4 is a storage device for storing data used in the biological state monitoring system 100 and, for example, can use a hard disk (magnetic disk) for that purpose.

The display unit 5 is monitor such as a liquid crystal monitor or the like for displaying information outputted from the control unit 3 to users of the biological state monitoring system 100.

The notifying unit 6 includes a device such as a speaker, for example, to auditorily perform a predetermined notification on the basis of the information from the control unit 3.

The input unit 7 is an interface for performing predetermined inputs for the control unit 3, which may be a keyboard and a mouse.

Note that inside the biological state monitoring system 100 having the above configuration, the part excluding the respiratory rate calculating unit 32 of the control unit 3 corresponds to the body motion determining system of this embodiment.

An explanation will be made on an operation of monitoring the biological state (presence or absence of a body motion and the respiratory rate) of the subject on the bed by using the biological state monitoring system 100 of such kind.

Figure 3:
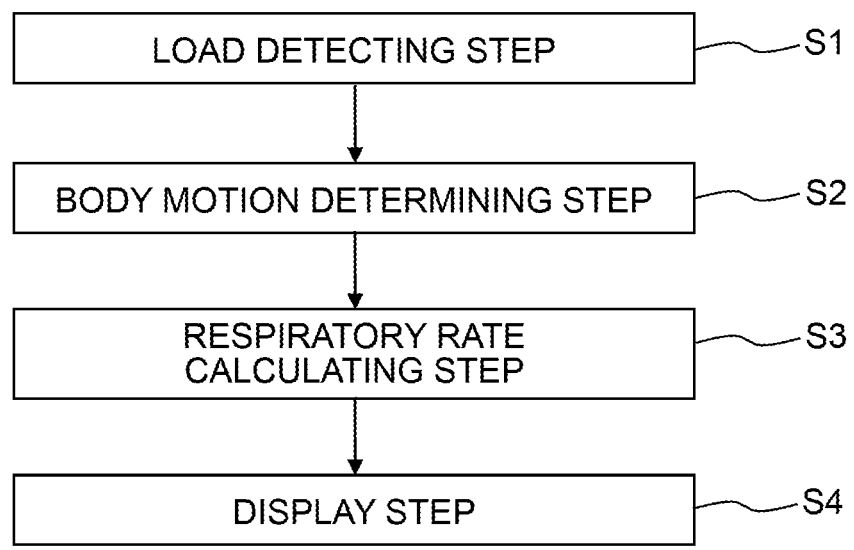
FIG. 3 is a flow chart depicting a method for monitoring a biological state by using the biological state monitoring system.

Monitoring the biological state of the subject by using the biological state monitoring system 100 includes: as depicted in the flow chart of FIG. 3, a load detecting step S1 for detecting the (body weight) load of the subject; a body motion determining step S2 for determining whether or not there is a body motion in the subject on the basis of the detected load; a respiratory rate calculating step S3 for calculating the respiratory rate of the subject with reference to whether or not there is a body motion in the subject; and a display step S4 for displaying the determination result of the body motion determining step S2 and/or the calculation result of the respiratory rate calculating step S3.

[The Load Detecting Step]

In the load detecting step S1, the load detectors 11, 12, 13, and 14 are used to detect the load of the subject S on the bed BD. The load of the subject S on the bed BD is applied dispersively to the load detectors 11 to 14 arranged respectively under the legs $BL_1$ to $BL_4$ of the bed BD at the four corners. The load of the subject S is detected dispersively by the four load detectors.

Each of the load detectors 11 to 14 detects the load (or variation of load), and outputs the result as an analog signal to the A/D converting unit 2. The A/D converting unit 2 converts the analog signal into a digital signal through a sampling period of 5 milliseconds, for example, and then outputs the digital signal (to be referred to below as "load signal") to the control unit 3. Hereinafter, the term "load signals $s_1$, $s_2$, $s_3$, and $s_4$" will be used to refer respectively to the load signals obtained, at the A/D converting unit 2, by converting the analog signals outputted from the load detectors 11, 12, 13, and 14 into the digital format.

[The Body Motion Determining Step]

In the body motion determining step S2, the body motion determining unit 31 uses at least one of the load signals $s_1$ to $s_4$, to determine whether or not there is a body motion in subject S.

In the present specification and in the present invention, the term "body motion" refers to any motion of the subject's head, torso (body-trunk), and/or four limbs. The body motion does not include motions of internal organs, blood vessels and the like along with the respirations, heartbeats, and the like. The body motion can be classified into a large body motion along with the motion of the subject S in the torso (body-trunk), and a small body motion along with the motion of the subject only in the four limbs, the head, and/or the like, as an example. One example of the large body motion is turn-over, sit-up or get-up, or the like, whereas one example of the small body motion is, a motion of the hands, the feet, the head or the like during sleep. When heartbeats, respirations and body motions arise in the subject, the load signals $s_1$ to $s_4$ from the load detectors 11 to 14 vary accordingly. The magnitude of variation increases in the order of the variation due to the heartbeats of the subject S, the variation due to the respirations of the subject S, the variation due to the small body motion of the subject S, and the variation due to the large body motion of the subject S.

Note that in the determination of a body motion of the subject described in the present specification and in the present invention, the magnitude of variation in the load signals $s_1$ to $s_4$ due to the heartbeats of the subject S is so small as neglectable. Therefore, in the present specification and in the present invention, the term "the subject only (merely) respires (or the subject merely performs a respiration)", and the load values and the load signals "vary due only to the respiration(s)" are used to mean that the subject has no body motion, and that the load values and the load signals show no variation due to the body motion; but not to mean that the subject does not have heartbeats, and that the load values and the load signals do not include the variation due to the heartbeats.

Figure 4:
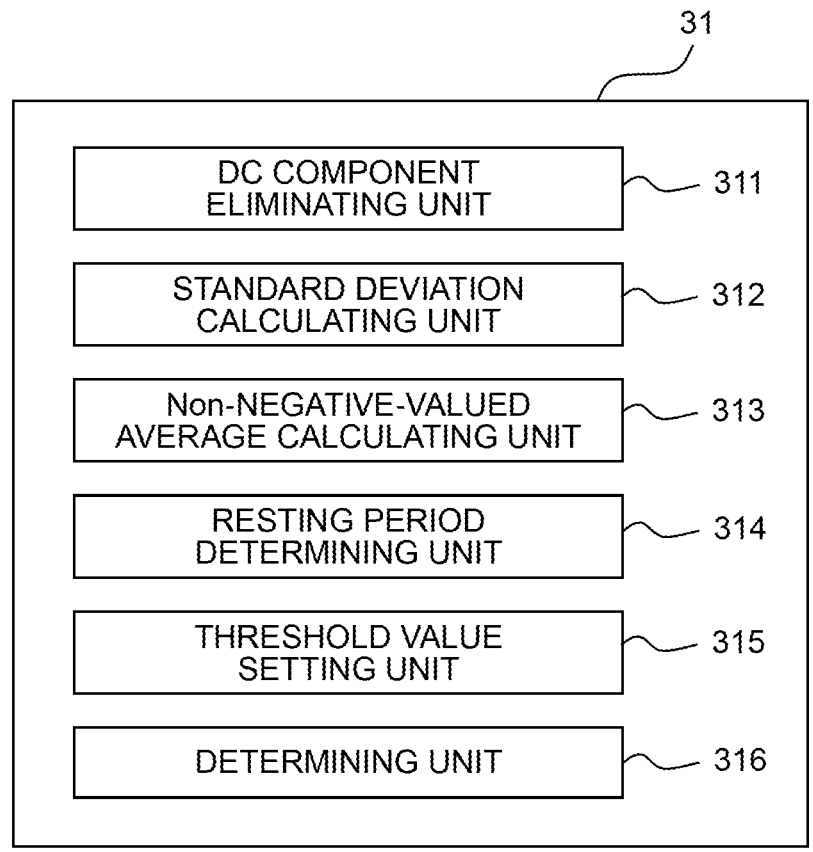
FIG. 4 is a block diagram depicting a specific configuration of a body motion determining unit.

As depicted in FIG. 4, the body motion determining unit 31 includes a DC (direct current) component eliminating unit 311, a standard deviation calculating unit 312, a non-negative-valued average calculating unit 313, a resting period determining unit 314, a threshold value setting unit 315, and a determining unit 316.

Figure 5:
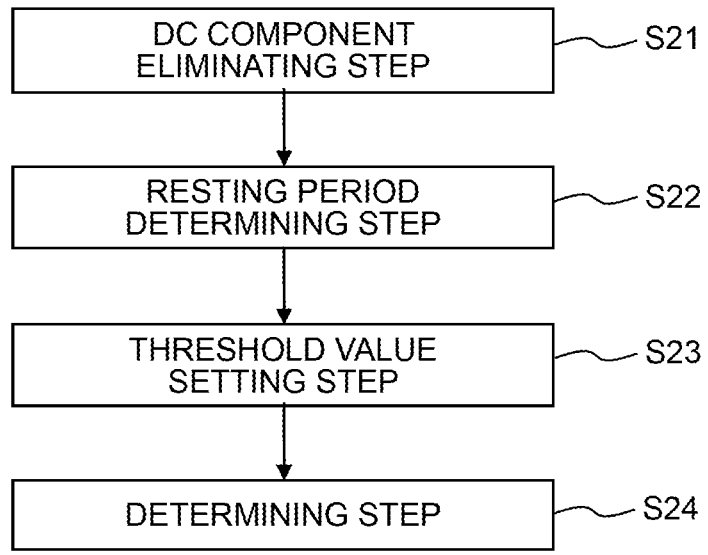
FIG. 5 is a flow chart depicting a procedure of a body motion determining step performed by the body motion determining unit.

The body motion determining step S2 includes, as depicted in FIG. 5, a DC component eliminating step S21, a resting period determining step S22, a threshold value setting step S23, and a determining step S24.

In the body motion determining step S2, the body motion determining unit 31 first carries out the DC component eliminating step S21 using the DC component eliminating unit 311 to eliminate the DC component from each of the load signals $s_1$ to $s_4$. The DC components are eliminated, in particular for example, by finding a motion average over a predetermined period (15 seconds for example) for each of the load signals $s_1$ to $s_4$, and then eliminating the found motion average from the sampling value of each of the load signals $s_1$ to $s_4$.

Hereinbelow, the signals obtained after the DC components are eliminated from the load signals $s_1$ to $s_4$ will be referred to as load signals $sc_1$ to $sc_4$.

The following steps, that is, the resting period determining step S22, the threshold value setting step S23 and the determining step S24, will be carried out using the load signals $sc_1$ to $sc_4$ obtained in the DC component eliminating step S21.

As a premise for carrying out the resting period determining step S22, the threshold value setting step S23 and the determining step S24, the body motion determining unit 31 constantly calculates a standard deviation σ with the standard deviation calculating unit 312, and constantly calculates a non-negative-valued average p with the non-negative-valued average calculating unit 313.

The standard deviation calculating unit 312 constantly calculates standard deviations $\sigma_1$ to $\sigma_4$ of the sampling values included in a predetermined sampling period (5 seconds for example) for each of the load signals $sc_1$ to $sc_4$ obtained in the DC component eliminating step S21.

Figure 6:
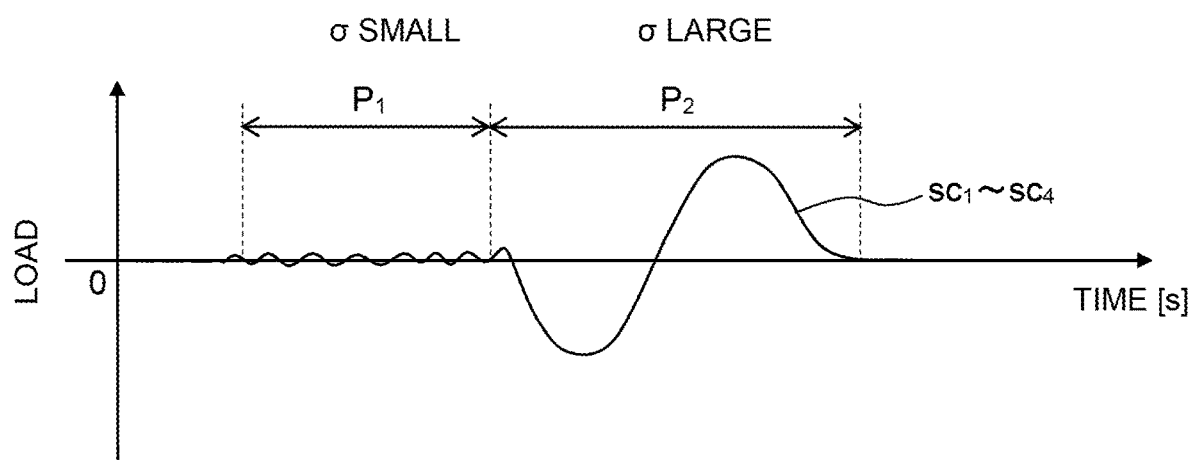
FIG. 6 is a schematic graph depicting an aspect of variation in load values detected by the load detectors in both a resting period when a subject only respires and a period when the subject is performing a body motion.

Because the standard deviation denotes the magnitude of variation in the sampling value, as depicted in FIG. 6, the standard deviations $\sigma_1$ to $\sigma_4$ become small during a period $P_1$ when the load signals $sc_1$ to $sc_4$ vary little whereas the standard deviations $\sigma_1$ to $\sigma_4$ become large during a period $P_2$ when the load signals $sc_1$ to $sc_4$ vary greatly.

The standard deviations $\sigma_1$ to $\sigma_4$ calculated in the standard deviation calculating unit 312 are used to determine a resting period (when the subject only respires without body motion) in the resting period determining step S22, and to determine whether or not the subject S has a body motion in the determining step S24, etc.

The non-negative-valued average calculating unit 313 constantly calculates non-negative-valued averages $\mu_1$ to $\mu_4$ of sampling values $W_{11}$ to $W_{14}$ included respectively in the predetermined sampling period (5 seconds for example) for the respective load signals $sc_1$ to $sc_4$ obtained in the DC component eliminating step S21.

An explanation will be made about a method for calculating the non-negative-valued average with an exemplary case of calculating the non-negative-valued average $\mu_1$ over the sampling period of 5 seconds for the load signal $sc_1$ outputted in the resting period.

Figure 7:
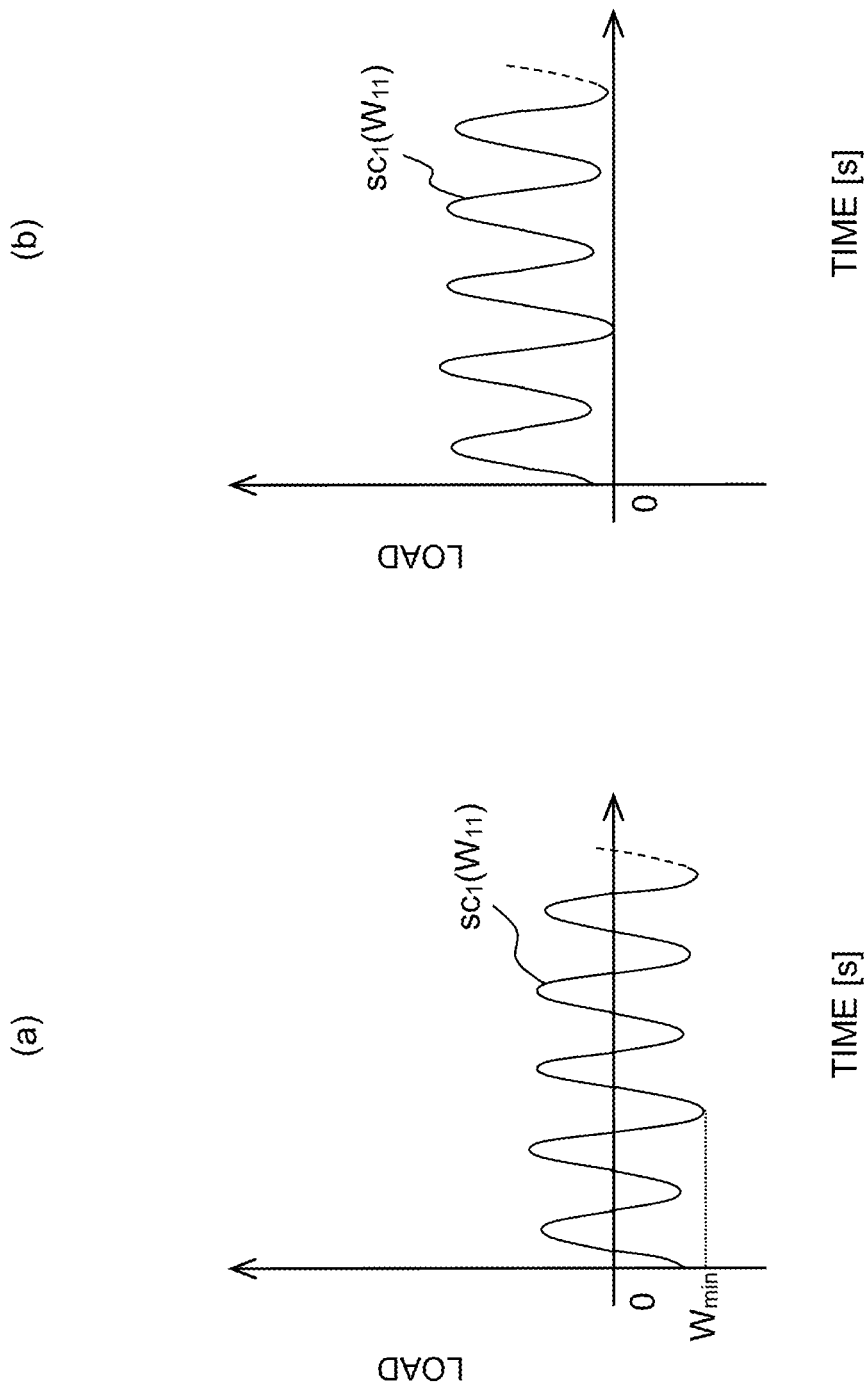

As depicted in FIG. 7(a), the load signal $sc_1$ oscillates or vibrates due only to the respiration of the subject S in the resting period (as described earlier on, the vibrating component due to the heartbeats is also included therein but is neglected for its smallness). In such load signal $sc_1$, the non-negative-valued average calculating unit 313 first specifies the minimal sampling value $W_{min}$ (negative) which is the minimum value of the sampling value $W_{11}$ included in that sampling period. Then, the non-negative-valued operation is made by subtracting the specified minimal sampling value $W_{min}$ from each sampling value $W_{11}$ within the sampling period (FIG. 7(*b*)).

Next, the non-negative-valued average calculating unit 313 calculates an average value of the respective sampling values $W_{11}$ having been non-negative-valued to acquire the non-negative-valued average pi. The non-negative-valued averages $\mu_2$ to $\mu_4$ are calculated in the same manner for the load signals $sc_2$ to $sc_4$.

The non-negative-valued averages $\mu_1$ to $\mu_4$ obtained in the resting period become large in a case that the amplitude of load variation due to the respiration of the subject S is large, but becomes small in a case that the amplitude of load variation due to the respiration of the subject S is small.

The non-negative-valued averages $\mu_1$ to $\mu_4$ calculated by the non-negative-valued average calculating unit 313 are used for setting a threshold value $\sigma_{th}$ in the threshold value setting step S23 (to be described in detail later on).

Returning to the flow chart of FIG. 5, in a case that the body motion determining unit 31 determines that a new subject S has arrived in the bed BD on the basis of an increase or the like of the load signals $s_1$ to $s_4$ (or the load signals $sc_1$ to $sc_4$), the body motion determining unit 31 carries out the resting period determining step S22 with the resting period determining unit 314 to determine that the subject S is situated in the resting period (the period when the subject only respires without body motion). This determination is carried out, in particular for example, by determining whether or not any of the standard deviations $\sigma_1$ to $\sigma_4$ calculated in the standard deviation calculating unit 312 is smaller than a predetermined threshold value $\sigma_0$.

Just as described above, the standard deviations $\sigma_1$ to $\sigma_4$ become small during the period when the load signals $sc_1$ to $sc_4$ vary little but become large during the period when the load signals $sc_1$ to $sc_4$ vary greatly. (FIG. 6). Therefore, any of the standard deviations $\sigma_1$ to $\sigma_4$ becomes small during a resting period when the subject S only respires without body motion (the period $P_1$ of FIG. 6, for example). Hence, if the threshold value $\sigma_0$ is set to a sufficiently small value, then when any one of the standard deviations $\sigma_1$ to $\sigma_4$ reaches the threshold value $\sigma_0$, it is possible to determine that the subject S is (situated) in the resting period.

Note that as will be described later on, there is difference among individuals in how small the variation in the load signals due to the respirations will become, in the resting period. Thus, in some subjects, it is still possible to maintain the standard deviations $\sigma_1$ to $\sigma_4$ at larger values than the threshold value $\sigma_0$ even during the resting period when they only respire without body motion. In such a case, for example, if the standard deviations $\sigma_1$ to $\sigma_4$ being kept at certain values being a little larger than the threshold value $\sigma_0$ through a predetermined period (5 to 10 seconds, for example), it is possible to determine that the subject is in the resting period. Because respirations generally give a certain rhythm, if the standard deviations $\sigma_1$ to $\sigma_4$ have certain small values to some degree over a predetermined period, then even with those values being a little larger than the threshold value $\sigma_0$, there is still a high possibility of that period falling into the resting period.

If the resting period determining step S22 determines that the subject S is in the resting period, then the body motion determining unit 31 causes the threshold value setting unit 315 to perform the threshold value setting step S23.

In the threshold value setting step S23, the threshold value setting unit 315 estimates the magnitude of a respiratory amplitude of the subject S and, based on the estimated magnitude of the respiratory amplitude, sets the threshold value $\sigma_{th}$ to be used in the determining step S24.

Figure 9:
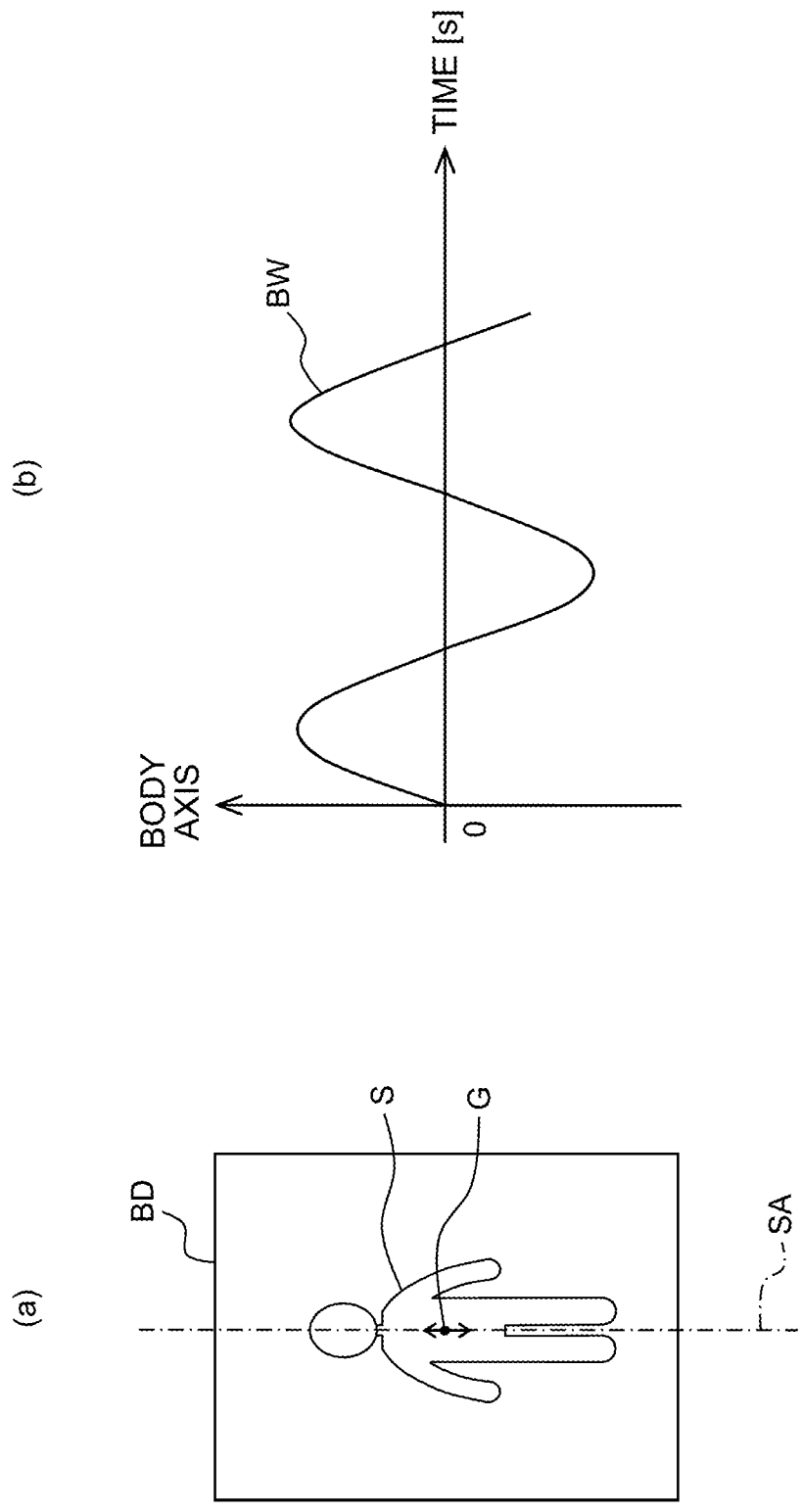
FIG. 9(a) is an illustrative view conceptionally depicting an aspect where the center of gravity of the subject oscillates or vibrates in a body axis direction of the subject according to the respiration of the subject.
FIG. 9(b) is a graph depicting an example of a respiratory waveform drawn on the basis of the oscillation of the center of gravity of the subject according to the respiration of the subject.

The respiratory amplitude of the subject S refers to the amplitude of vibration (oscillation) of the center of gravity G of the subject S due to the respiration of the subject S. As described in the specification of Japanese Patent No. 6105703, the position of the center of gravity G of the subject S vibrates (oscillates) along the extending direction of the body axis SA of the subject S (the extending direction of the backbone of the subject S) according to the respiration of the subject S (FIG. 9(*a*)). The respiratory amplitude of the subject S refers to the amplitude of this vibration.

The threshold value setting unit 315 selects any one of the non-negative-valued averages $\mu_1$ to $\mu_4$ calculated by the non-negative-valued average calculating unit 313 in the resting period determined in the resting period determining step S22 and, according to the magnitude of the selected value, estimates the magnitude of the respiratory amplitude of the subject S. It can be said that if the non-negative-valued averages $\mu_1$ to $\mu_4$ in the resting period are large (or small), then the amplitudes of the oscillations of the load signals $s_1$ to $s_4$ and $sc_1$ to $sc_4$, due to the respiration of the subject S, are large (or small). Therefore, the respiratory amplitude of the subject S is also estimated as large (or small).

Next, the threshold value setting unit 315 sets the threshold value $\sigma_{th}$ to be used in the determining step S24 on the basis of the estimated magnitude of the respiratory amplitude of the subject S. In particular, for example, in a case that the estimated magnitude of the respiratory amplitude is larger than a predetermined threshold value $\mu_{th}$, then the threshold value $\sigma_{th}$ is set to a first threshold value $\sigma_{th1}$, whereas in a case that the estimated magnitude of the respiratory amplitude is smaller than the predetermined threshold value $\mu_{th}$, then the threshold value $\sigma_{th}$ is set to a second threshold value $\sigma_{th2}$ ($<\sigma_{th1}$). A description will be made later on about the reason of changing the magnitude of the threshold value $\sigma_{th}$ according to the magnitude of the respiratory amplitude of the subject S in this manner.

Note that without estimating the magnitude of the respiratory amplitude, any one of the calculated non-negative-valued averages $\mu_1$ to $\mu_4$ (a selected non-negative-valued average $\mu_s$) may be compared with the threshold value $\mu_{th}$. Then, in a case that $\mu_s$ is larger than the threshold value $\mu_{th}$, then the threshold value $\sigma_{th}$ may be set to the first threshold value $\sigma_{th1}$, whereas in a case that $\mu_s$ is smaller than the threshold value $\mu_{th}$, then the threshold value $\sigma_{th}$ may be set to the second threshold value $\sigma_{th2}$ ($<\sigma_{th1}$). In this case, substantially, the threshold value $\sigma_{th}$ is also set on the basis of the magnitude of the respiratory amplitude of the subject S.

Thereafter, the body motion determining unit 31 uses the set threshold value $\sigma_{th}$ to perform the determining step S24 with the determining unit 316, so as to determine whether or not the subject S has a body motion. Thereafter, the body motion determining unit 31 may perform the determining step S24 alone but not perform the resting period determining step S22 and the threshold value setting step S23, under a condition that the body motion determining unit 31 continuously use the threshold value $\sigma_{th}$ until the subject S leaves the bed BD.

Whether or not the subject S has a body motion (whether the body of the subject presents or not) is determined, in particular for example, by comparing the threshold value $\sigma_{th}$ set in the threshold value setting step S23 with any one of the standard deviations $\sigma_1$ to $\sigma_4$ (to be referred to below as "selected standard deviation $\sigma_s$") of the load signals $sc_1$ to $sc_4$ calculated constantly by the standard deviation calculating unit 312.

During the period when the subject S has a body motion, the variation of the load signals $sc_1$ to $sc_4$ increases in magnitude, so that the standard deviations $\sigma_1$ to $\sigma_4$ and, consequently, the selected standard deviation $\sigma_s$ also increase (for example, during the period $P_2$ of FIG. 6). Therefore, the selected standard deviation $\sigma_s$ is compared with the set threshold value $\sigma_{th}$ (that is, the $\sigma_{th1}$ or the $\sigma_{th2}$) to determine that the subject S has a body motion in a case that the selected standard deviation $\sigma_s$ becomes larger than the threshold value $\sigma_{th}$.

In this context, a description will be made as follows on the reason for the body motion determining unit 31 of this embodiment to set the threshold value $\sigma_{th}$ which differs according to each subject S by taking the magnitude of the respiratory amplitude of the subject S into referential consideration.

As described earlier on, the load signals $s_1$ to $s_4$ from the load detectors 11 to 14 vary according to the heartbeats, respirations and body motion of the subject S, and the magnitude of the variation changes according to the physical characteristic of the subject S (such as the height, weight, body fat percentage, muscle mass, and the like). Then, according to the discovery and knowledge of the inventor of the present invention, there is a certain correlation between the magnitude (amount) of the load variation according to respirations (the magnitude of respiratory amplitude) and the magnitude (amount) of load variation according to the body motion.

Figure 8:
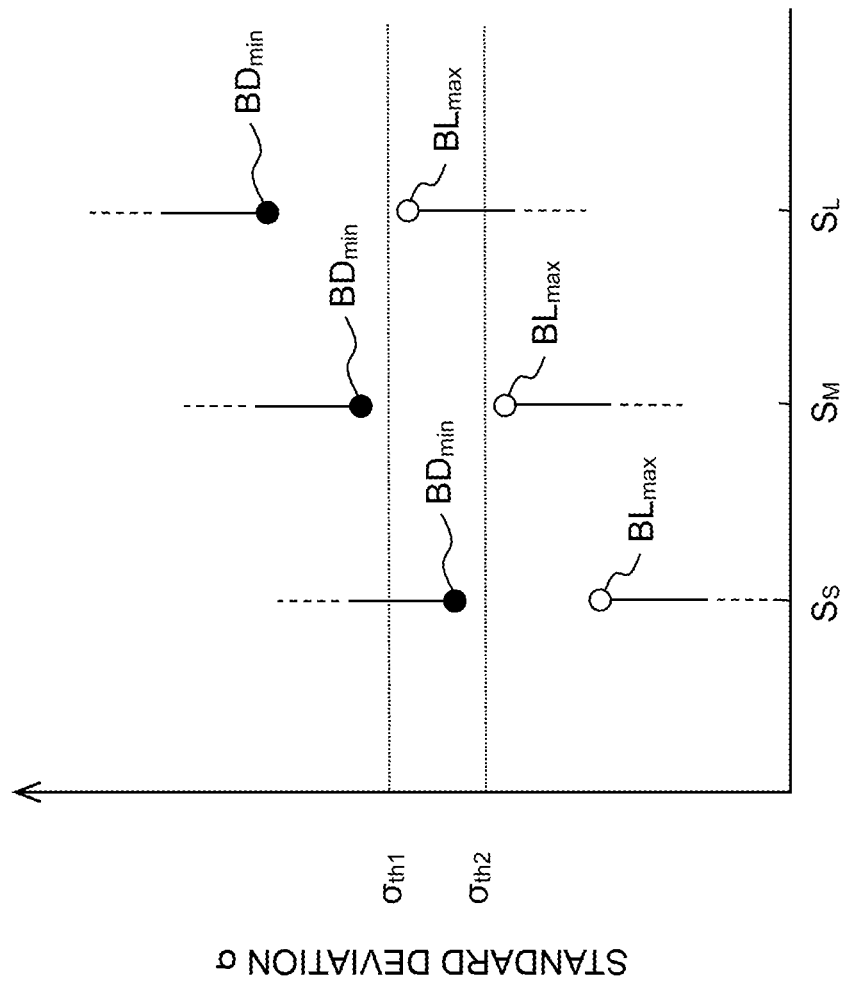
FIG. 8 is a graph schematically depicting the magnitude of variation (standard deviation) in the detection value of the load detector due to the respiration of the subject and the magnitude of variation (standard deviation) in the detection value of the load detector due to a small body motion of the subject, with respect to each of a subject whose respiratory amplitude is small, a subject whose respiratory amplitude is about average, and a subject whose respiratory amplitude is large.

FIG. 8 is a graph schematically depicting such an aspect. In FIG. 8, the open circles show the upper limit values (the respiratory variation upper limit $BL_{max}$) of the magnitude of load variation which can be exhibited according to the respiration of the subject S (shown in FIG. 8 with the standard deviation), while the filled circles show the lower limit values (the body motion variation lower limit $BD_{min}$) of the magnitude of load variation which can be exhibited according to the body motion (small body motion) of the subject.

As shown in FIG. 8, the respiratory variation upper limit $BL_{max}$ and the body motion variation lower limit $BD_{min}$ of a subject $S_S$ with a small respiratory amplitude are, respectively, smaller than the respiratory variation upper limit $BL_{max}$ and the body motion variation lower limit $BD_{min}$ of a subject $S_M$ with the average respiratory amplitude. On the other hand, the respiratory variation upper limit $BL_{max}$ and the body motion variation lower limit $BD_{min}$ of a subject $S_L$ with a large respiratory amplitude are, respectively, larger than the respiratory variation upper limit $BL_{max}$ and the body motion variation lower limit $BD_{min}$ of the subject $S_M$ with the average respiratory amplitude.

In this context, according to the discovery and knowledge of the inventor of the present invention, as shown in FIG. 8, the respiratory variation upper limit $BL_{max}$ of the subject $S_L$ with the large amplitude may become larger than the body motion variation lower limit $BD_{min}$ of the subject $S_S$ with the small respiratory amplitude. Therefore, it is difficult to use a single threshold value alone for determining the body motion of the subject $S_S$ with the small respiratory amplitude and for determining the body motion of the subject $S_L$ with the large respiratory amplitude, at a high precision.

That is, suppose that the $\sigma_{th1}$ (FIG. 8), which is larger than the respiratory variation upper limit $BL_{max}$ of the subject $S_L$ but smaller than the body motion variation lower limit $BD_{min}$ of the subject $S_L$, is used so as to correctly determine the body motion of the subject $S_L$ with the large respiratory amplitude. Then, it is possible to correctly determine the body motion of the subject $S_L$ but, for the subject $S_S$ with the small respiratory amplitude, when the subject $S_S$ has a slight body motion, such a mistaken determination may be made that there is no body motion in the subject $S_S$.

Conversely, suppose that the $\sigma_{th2}$ (FIG. 8), which is larger than the respiratory variation upper limit $BL_{max}$ of the subject $S_s$ but smaller than the body motion variation lower limit $BD_{min}$ of the subject $S_s$, is used so as to correctly determine the body motion of the subject $S_s$ with the small respiratory amplitude. Then, it is possible to correctly determine the body motion of the subject $S_s$ but, for the subject $S_L$ with the larger respiratory level, when the subject $S_L$ only respires, such a mistaken determination may be made that there is a body motion in the subject $S_L$.

In the biological state monitoring system 100 of this embodiment, however, based on the magnitude of the respiratory amplitude of the subject S, the threshold value $\sigma_{th}$ is set according to a specific subject S, and the set threshold value $\sigma_{th}$ is used to determine whether or not there is a body motion in the subject S. By virtue of this, it is possible to determine at a high precision whether or not there is a body motion in each of a plurality of subjects S who differ in the magnitude of the respiratory amplitude.

[Respiratory Rate Calculating Step]

In the respiratory rate calculating step S3, the respiratory rate calculating unit 32 calculates the respiratory rate of the subject S on the basis of at least one of the load signals $s_1$ to $s_4$.

In particular, for example, the respiratory rate calculating unit 32 calculates the respiratory rate of the subject S by carrying out the Fourier analysis on at least one of the load signals $s_1$ to $s_4$ (or the load signals $sc_1$ to $sc_4$) so as to specify the peak frequency coming up in the frequency band corresponding to the respiration (from about 0.2 Hz to about 0.33 Hz because the human respiration is performed about 12 to 20 times per minute). With the specified peak frequency, it is possible to calculate (estimate) the respiratory rate of the subject S over that period.

Further, in the period when the subject S has a body motion (the period $P_2$ of FIG. 6 for example), the load signals $s_1$ to $s_4$ and $sc_1$ to $sc_4$ vibrate at a different frequency from that of the vibration due to the respiration of the subject S (or no vibration is exhibited), unlike the period when the subject S only respires (the period $P_1$ of FIG. 6 for example). Therefore, even if the Fourier analysis is applied to the load signals $s_1$ to $s_4$ and $sc_1$ to $sc_4$ obtained in such period, it is difficult to correctly calculate the respiratory rate of the subject S.

Therefore, the respiratory rate calculating unit 32 of this embodiment ceases to calculate the respiratory rate for the period in which the subject S has a body motion, on the basis of the determination result of the body motion determining unit 31. As for the respiratory rate of this period, an estimation value may be outputted on the basis of the respiratory rate of periods before and/or after such period, or a message may be outputted to indicate that the respiratory rate is unknown.

[Display Step]

In the display step S4, the control unit 3 causes the display unit 5 to display the determination result of the body motion determining step S2 and/or the calculation result of the respiratory rate calculating step S3. Further, in the display step S4, the notifying unit 6 may be used to perform a notification in addition to or instead of the display using the display unit 5. In this case, for example, when the subject S has a body motion, a notification sound may be emitted to notify the nurses, caregivers and/or others who are the users of the biological state monitoring system 100 that a body motion is arising.

The effects of the body motion determining system and the biological state monitoring system 100 including the same according to this embodiment are summarized as follows.

In the body motion determining system and the biological state monitoring system 100 including the same according to this embodiment, the body motion determining unit 31 sets a suitable threshold value $\sigma_{th}$ for each subject S on the basis of the respiratory amplitude of the subject S, and uses the set threshold value to determine whether or not the subject S has a body motion. Hence, it is possible to determine whether or not there is a body motion at a high precision for each of a plurality of subjects S who differ in the magnitude of the respiratory amplitude.

In the biological state monitoring system 100 of this embodiment, based on the determination result of the body motion determining unit 31, the respiratory rate calculating unit 32 excludes the periods difficult in calculating the respiratory rate of the subject S from the objects of calculating the respiratory rate. Therefore, there is a high reliability of the respiratory rate of the subject S calculated by the respiratory rate calculating unit 32.

The body motion determining system and the biological state monitoring system 100 including the same according to this embodiment use the load detectors 11 to 14 arranged under the legs $BL_1$ to $BL_4$ of the bed BD to monitor the biological state of the subject S. Therefore, it is not necessary to attach any measuring device to the body of the subject S so that the subject S will not feel discomfort and a sense of incongruity.

Modified Embodiments

It is also possible to adopt the following modified embodiments with respect to the body motion determining system and the biological state monitoring system 100 according to the above embodiment.

In the body motion determining unit 31 of the above embodiment, each time the determining unit 316 determines that the subject S has a body motion in the determining step S24, the resting period determining step S22 and the threshold value setting step S23 may be performed again to reset the threshold value $\sigma_{th}$ for the use in the determining step S24.

The magnitude of the respiratory amplitude of the subject S depends basically on the physical characteristic of the subject S so as not to change greatly during the monitoring period. Therefore, generally speaking, as far as there is no change in the subject S, it is possible to use the threshold value $\sigma_{th}$, which is once set in the threshold value setting step S23, continuously in the successive monitoring.

However, patients, et al. who are receiving terminal cares (end-of-life medical treatment and end-of-life care) often exhibit change in physical condition as significant as the respiratory amplitude is changed, and such kind of change in physical condition often arises along with a body motion. Therefore, for the patients, et al. who are receiving terminal cares, it is possible to reset the threshold value $\sigma_{th}$ at each body motion and use the threshold value $\sigma_{th}$ according to the physical condition on each occasion, so as to raise the precision of determining the body motion, thereby upgrading the reliability of the calculated respiratory rate.

On the other hand, the non-negative-valued average calculating unit 313 of the body motion determining unit 31 of the above embodiment may cease to calculate the non-negative-valued averages $\mu_1$ to $\mu_4$ after the threshold value $\sigma_{th}$ is set, in a case that the threshold value $\sigma_{th}$ once set is to be used continuously in the determining step S24. Alternatively, the non-negative-valued averages $\mu_1$ to $\mu_4$ may be calculated only in the case where the resting period determining unit 314 determines that the subject S is in the resting period, in the resting period determining step S22.

In the above embodiment, the standard deviation calculating unit 312 of the body motion determining unit 31 may calculate dispersions $\sigma^2_1$ to $\sigma^2_4$ instead of or in addition to the standard deviations $\sigma_1$ to $\sigma_4$. In this case, in the threshold value setting step S23, a threshold value $\sigma^2_{th}$ according to the dispersions $\sigma^2_1$ to $\sigma^2_4$ is set. Further, in the determining step S24, whether or not the subject S has a body motion is determined by comparing the threshold value $\sigma^2_{th}$ to any one or the sum of any two or more of the dispersions $\sigma^2_1$ to $\sigma^2_4$.

In the above embodiment, the body motion determining unit 31 compares whether or not any one of the standard deviations $\sigma_1$ to $\sigma_4$ is smaller than the predetermined threshold value $\sigma_0$, to determine that the subject S is in the resting period. However, without being limited to that, the body motion determining unit 31 may compare the sum of any two or more of the standard deviations $\sigma_1$ to $\sigma_4$ with the threshold value, to determine that the subject S is in the resting period.

In the above embodiment, the body motion determining unit 31 selects any one of the non-negative-valued averages $\mu_1$ to $\mu_4$ and, based on that one, estimates the magnitude of the respiratory amplitude of the subject S. However, without being limited to that, the body motion determining unit 31 may estimate the magnitude of the respiratory amplitude of the subject S on the basis of the sum of any two or more of the non-negative-valued averages $\mu_1$ to $\mu_4$. For example, by using the summation of the non-negative-valued averages $\mu_1$ to $\mu_4$, it is possible to estimate the magnitude of the respiratory amplitude of the subject S at a high precision regardless of the position of the subject S on the bed BD.

In the above embodiment, the body motion determining unit 31 sets the threshold value $\sigma_{th}$ to either the first threshold value $\sigma_{th1}$ or the smaller second threshold value $\sigma_{th2}$. However, without being limited to that, the body motion determining unit 31 may set the threshold value $\sigma_{th}$ in a more detailed manner according to the magnitude of the respiratory amplitude of the subject S estimated from the non-negative-valued averages $\mu_1$ to $\mu_4$. In particular, the threshold value $\sigma_{th}$ may be set to any of the first threshold value $\sigma_{th1}$ to an nth threshold value $\sigma_{thn}$ (n is a natural number larger than two) which are different from one another.

In the above embodiment, the body motion determining unit 31 compares the set threshold value $\sigma_{th}$ to the selected standard deviation $\sigma_s$ which is any one of the standard deviations $\sigma_1$ to $\sigma_4$, to determine whether or not the subject S has a body motion. However, without being limited to that, the body motion determining unit 31 may determine whether or not the subject S has a body motion by comparing the threshold value $\sigma_{th}$ with the sum of any two or more of the standard deviations $\sigma_1$ to $\sigma_4$. Note that in this case, the threshold value $\sigma_{th}$ set in the threshold value setting step S23 is supposed to also accord to the contents of the standard deviations used in the determining step S24.

In the above embodiment, the body motion determining unit 31 may include a center of gravity position calculating unit instead of or in addition to the standard deviation calculating unit 312. The center of gravity position calculating unit uses sampling values $W_{11}$ to $W_{14}$ of the load signals $s_1$ to $s_4$ (or the load signals $sc_1$ to $sc_4$) from the load detectors 11 to 14, to calculate the position (X, Y) of the center of gravity G of the subject S.

The calculation of the position (X, Y) of the center of gravity G is performed in accordance with the following operation. Coordinates X-Y are set up for the bed BD as depicted in FIG. 2, and the coordinates of the load detectors 11, 12, 13, and 14 are supposed to be: $(X_{11}, Y_{11})$, $(X_{12}, Y_{12})$, $(X_{13}, Y_{13})$, and $(X_{14}, Y_{14})$, respectively. Then, the center of gravity position G (X, Y) of the load applied on the bed BD is calculated with the following formulas.

$$X = \frac{X_{11} \times W_{11} + X_{12} \times W_{12} + X_{13} \times W_{13} + X_{14} \times W_{14}}{W_{11} + W_{12} + W_{13} + W_{14}} \quad \text{(Formula 1)}$$

and $$Y = \frac{Y_{11} \times W_{11} + Y_{12} \times W_{12} + Y_{13} \times W_{13} + Y_{14} \times W_{14}}{W_{11} + W_{12} + W_{13} + W_{14}} \quad \text{(Formula 2)}$$

The center of gravity position calculating unit finds a temporal variation of the position (X, Y) of the center of gravity G, i.e., a center of gravity locus GT while calculating the position (X, Y) of the center of gravity G at a predetermined sampling period T on the basis of the formulas 1 and 2 given above. The acquired center of gravity locus GT is stored, for example, in the storage unit 4.

Here, the movement of the center of gravity G of the subject S is characterized as follows.

As described earlier on, the center of gravity G of the subject S vibrates in the direction of the body axis SA of the subject S according to the respirations of the subject S (FIG. 9(a)). Further, when the subject S has a small body motion or a large body motion, the center of gravity G of the subject S moves according to the body motion. Then, the moving distance of the center of gravity G over a predetermined period increases in the ascending order of the period when the subject S only respires, the period when the subject S has a small body motion, and the period when the subject S has a large body motion.

Therefore, the body motion determining unit 31 can determine whether or not the subject S has a body motion by comparing a predetermined threshold value with the moving distance of the center of gravity G over a predetermined period. In particular, for example, it is possible to determine that the subject S has a small body motion if the moving distance D of the center of gravity G over a predetermined period is longer than a threshold value $D_{th}$.

In this modified embodiment, too, the body motion determining unit 31 causes the threshold value setting unit 315 to perform the threshold value setting step S23 to set the threshold value $D_{th}$ according to the magnitude of the respiratory amplitude of the subject S (for example, either a $D_{th1}$ or a $D_{th2}$ smaller than the $D_{th1}$).

In the above embodiment, the respiratory rate calculating unit 32 calculates the respiratory rate of the subject S by performing the Fourier transform on at least one of the load signals $s_1$ to $s_4$ (or the load signals $sc_1$ to $sc_4$). However, the present invention is not limited to that.

In particular, for example, if the body motion determining unit 31 has the center of gravity position calculating unit, then it is possible to draw a respiratory waveform BW of the subject S (FIG. 9(b)) from the calculated position of the center of gravity G. The respiratory waveform BW is drawn with the direction of the body axis SA as the vertical axis and with the time axis as the horizontal axis, by plotting, on the vertical axis, the distance between the position obtained by projecting the position (X, Y) of the center of gravity G on the body axis SA at each time, and the oscillation center of the oscillation of the center of gravity G due to the respiration. The respiratory rate calculating unit 32 can regard the oscillation rate of the respiratory waveform BW drawn in this manner as the respiratory rate of the subject S.

Note that in this case, too, when the subject S has a body motion, the center of gravity G of the subject S moves greatly to deviate from the oscillation due to the respirations, so that the respiratory waveform BW also departs from the state of being oscillating due only to the respirations. Therefore, when the body motion determining unit 31 determines that the subject S has a body motion, calculation of the respiratory rate is ceased.

In the above embodiment, the control unit 3 may display the drawn respiratory waveform BW on the display unit 5.

In the above embodiment, the body motion determining unit 31 first determines that the subject S is in the resting period in the resting period determining step S22, and then uses the non-negative-valued average p in that period to estimate the magnitude of the respiratory amplitude of the subject S. However, the present invention is not limited to that.

The subject S rarely moves (give rise to a body motion) constantly on the bed BD, but, usually, the subject S is resting without body motion (only respiring) during the most part of the period of his/her being present on the bed BD. Therefore, if the non-negative-valued averages $\mu_1$ to $\mu_4$ are observed continuously over a predetermined period of time (one minute or longer for example) without determining the resting period, then the minimal value of any one of (or the sum of any two or more of) the non-negative-valued averages $\mu_1$ to $\mu_4$ obtained sequentially in that period is often substantially a value obtainable in the resting period (in other words, although the resting period is not distinctly determined, in many cases, the subject is in the resting state at the point when that minimal value is obtained, and thus the obtained minimal value is the non-negative-valued average in the resting period). In this manner, the body motion determining unit 31 may estimate the magnitude of the respiratory amplitude of the subject S on the basis of the minimal value of the non-negative-valued averages obtained sequentially in the predetermined period.

Further, in this case, if it is observed a value even smaller than the minimal value of the non-negative-valued averages once obtained, then on the basis of such value, the magnitude of the respiratory amplitude of the subject S may be estimated anew and/or the threshold value $\sigma_{th}$ be set anew as necessary.

Alternatively, it is possible to carry out the Fourier analysis on the load signals $s_1$ to $s_4$ (or the load signals $sc_1$ to $sc_4$) from the load detectors $s_{11}$ to $s_{14}$ to extract only the signals of the respiration band, and to estimate the magnitude of the respiratory amplitude of the subject S from the non-negative-valued average calculated on the basis of the extracted signals. According to this method, because it is possible to exclude the influence of body motion on the load signals $s_1$ to $s_4$ (or the load signals $sc_1$ to $sc_4$) by way of the Fourier analysis, the magnitude of the respiratory amplitude of the subject S can be estimated at any time without determining the resting period.

In the above embodiment and modified embodiments, as an example of the method for estimating the magnitude of the respiratory amplitude of the subject S on the basis of the non-negative-valued average p, it is possible to regard the same magnitude or predetermined multiples of the magnitude of the non-negative-valued average p as the magnitude of the respiratory amplitude of the subject S.

In the above embodiment, the body motion determining unit 31 can also find the respiratory amplitude of the subject S without using the non-negative-valued average p.

In particular, for example, if there is a center of gravity position calculating unit and the respiratory waveform BW is drawn, then it is possible to estimate (determine) the respiratory amplitude of the subject S from the amplitude of the respiratory waveform BW. Alternatively, it is possible to estimate (determine) the respiratory amplitude of the subject S on the basis of at least one of the amplitudes of the load signals $s_1$ to $s_4$ and the load signals $sc_1$ to $sc_4$ in the resting period.

The biological state monitoring system 100 of the above embodiment may further include a biological state determining unit to determine biological state(s) different from whether or not the subject S has a body motion and the respiratory rate of the subject S. Such a biological state determining unit determines, for example, whether the subject S is present in or absent from the bed, asleep or awake, dead or alive, etc., on the basis of whether or not the subject S has a body motion, the respiratory rate of the subject S, etc.

Because the biological state monitoring system 100 of the above embodiment can determine the body motion of the subject S and estimate the respiratory rate of the subject S at a high precision, the biological state monitoring system 100 of the modified embodiments based on the former can also determine whether the subject S is present in or absent from the bed, asleep or awake, dead or alive, etc., at a high precision.

The biological state monitoring system 100 of the above embodiment does not need to include all of the load detectors 11 to 14 but may include only any one of the four. Further, the load detectors do not need to be arranged at the four corners of the bed but may be arranged in any positions such that they can detect the load of the subject on the bed and the variation thereof. Further, the load detectors 11 to 14 are not limited to load sensors using beam-type load cells but, for example, force sensors are also usable.

Figure 10:
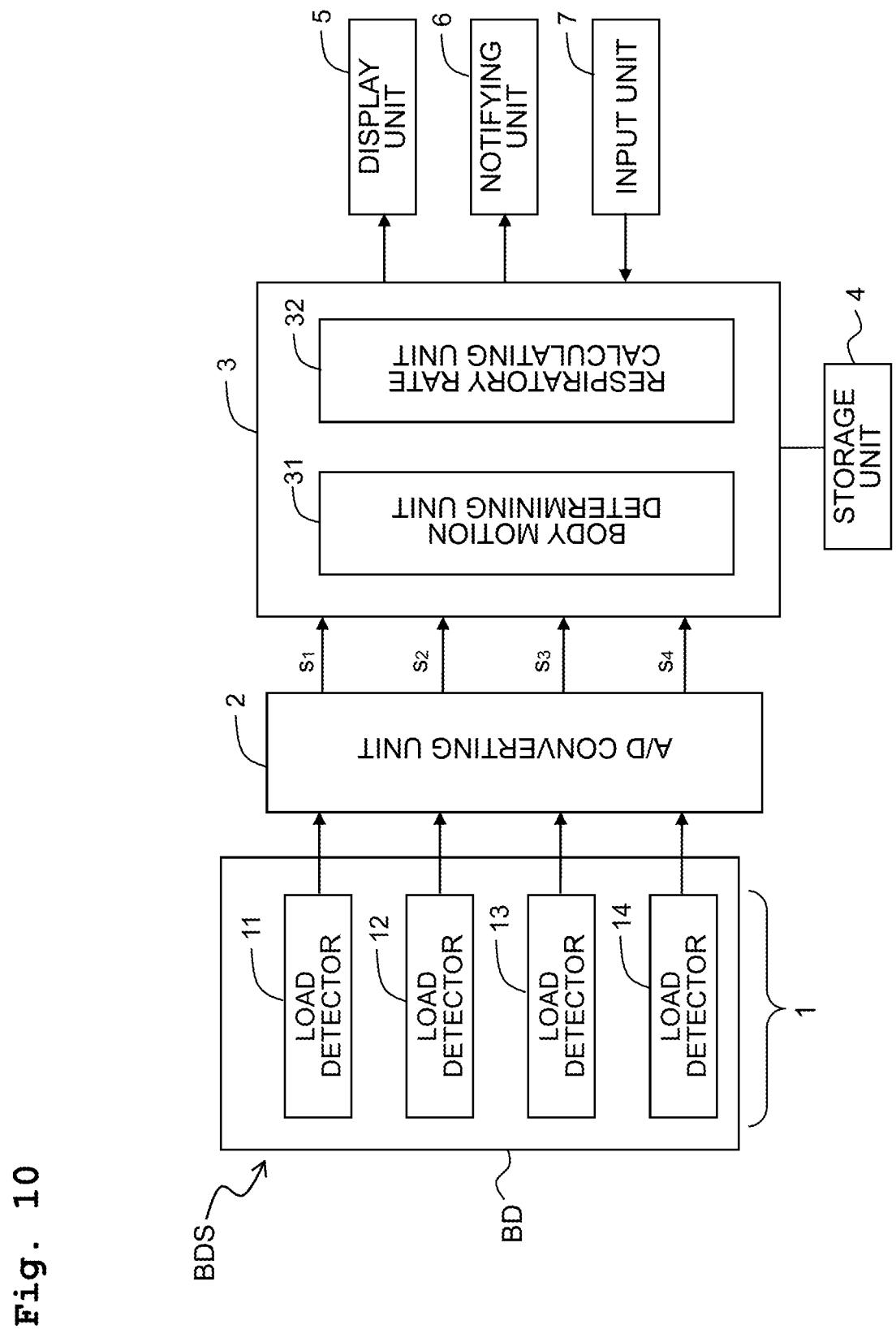
FIG. 10 is a block diagram depicting an overall configuration of a bed system according to a modified embodiment of the present invention.

In the biological state monitoring system 100 of the above embodiment, the load detectors 11 to 14 are arranged respectively on the undersides of the casters C attached to the lower ends of the legs of the bed BD. However, there is no limitation thereto. Each of the load detectors 11 to 14 may be provided respectively between each of the four legs of the bed BD and the board of the bed BD. Alternatively, if each of the four legs of the bed BD can be divided into upper and lower portions, each of the load detectors 11 to 14 may be provided between each of the upper legs and each of the lower legs. Further alternatively, the load detectors 11 to 14 may be formed integral with or removable from the bed BD to construct a bed system BDS comprising the bed BD, and the body motion determining system or the biological state monitoring system 100 of this embodiment (FIG. 10).

In the biological state monitoring system 100 of the above embodiment, between the load detecting unit 1 and the A/D converting unit 2, it is possible to provide a signal amplifying unit to amplify the load signals from the load detecting unit 1, and a filtering unit to eliminate the noises from the load signals.

In the biological state monitoring system 100 of the above embodiment, the display unit 5 may include a simplified visible display means such as a printer for printing out information showing the biological state, a lamp displaying the biological state, and/or the like, instead of the monitor or in addition to the monitor. Further, the notifying unit 6 may include a vibration generating unit for carrying out the notification by way of vibration, instead of the speaker or in addition to the speaker.

The present invention is not limited to the embodiment described above provided that the feature of the present invention is maintained. Other embodiments, which are conceivable within the scope of the technical concept of the present invention, are also included in the scope of the present invention.

INDUSTRIAL APPLICABILITY

According to the biological state monitoring system of the present invention, it is possible to determine whether or not the subject has a body motion and determine the respiratory rate of the subject at a high precision for subjects having any kind of physical characteristic. Therefore, by using the biological state monitoring system of the present invention, it is possible to provide high-quality medical treatments and caregiving services on the basis of those high-precision determinations.

PARTS LIST

1: load detecting unit, 11, 12, 13, 14: load detector, 2: A/D converting unit, 3: control unit, 31: body motion determining unit, 32: respiratory rate calculating unit 32, 4: storage unit, 5: display unit, 6: notifying unit, 7: input unit, 100: biological state monitoring system, BD: bed, BDS: bed system, S: subject.

What is claimed is:
1. A body motion determination system for determining whether a body motion of a subject on a bed presents or not, the system comprising:
 a load detector configured to detect a load of the subject on the bed;
 a display; and
 a controller configured to control the body motion determination system to:
 calculate non-negative-valued averages of a detection value of the load detector continuously in a period;
 set a threshold value to be used in determining whether the body motion of the subject presents or not, based on a minimum value of the non-negative-valued averages calculated in the period;
 calculate a standard deviation of the detection value of the load detector;
 determine whether the body motion of the subject presents or not based on a comparison between the calculated standard deviation and the threshold value; and
 cause the display to display a result of the determining of whether the body motion of the subject presents or not to a user of the system, or cause an auditory device to perform a notification based on the result of the determining of whether the body motion of the subject presents or not,
 wherein the controller is further configured:
 to newly set the threshold value when the controller determines that the body motion of the subject presents, based on the minimum value of the non-negative-valued averages calculated in the period after a determination that the body motion of the subject presents; and then continue to use the newly set threshold value until the controller determines that the body motion of the subject presents next and another threshold value is determined.

2. The body motion determination system according to claim 1, wherein the controller is further configured to determine that a period in which the standard deviation is not more than a predetermined value is a resting period in which the subject merely performs a respiration, and wherein
the controller sets the threshold value based on the non-negative-valued average calculated in the resting period determined by the controller.

3. The body motion determination system according to claim 1, wherein:
the load detector is configured to detect the load of the subject on the bed to successively obtain a plurality of detection values;
the calculating of the non-negative-valued average of the detection value of the load detector includes calculating a non-negative-valued average of the plurality of detection values obtained in a sampling period;
the calculating of the standard deviation of the detection value of the load detector includes calculating a standard deviation of the plurality of detection values; and
the calculating of the non-negative-valued average of the plurality of detection values obtained in the sampling period includes subtracting a minimum value of the plurality of detection values obtained in the sampling period from each of the plurality of detection values obtained in the sampling period, the minimum value being a negative value.

4. A biological state monitoring system for monitoring a biological state of a subject on a bed, the system comprising:
a body motion determining system as defined in claim 1; wherein
the controller is further configured to calculate a respiratory rate of the subject based on the detection value of the load detector, and wherein
the controller ceases calculating of the respiratory rate during a period for which the body motion determining system determines that the body motion of the subject presents.

5. The biological state monitoring system according to claim 4, wherein the controller is further configured to perform at least one of a present-in or absent-from the bed determination of the subject, an asleep or awake determination of the subject, and a dead or alive determination of the subject, based on a determination result of the body motion determination system and/or the respiratory rate of the subject calculated by the controller.

6. A bed system comprising:
a bed; and
the body motion determining system as defined in claim 1.

7. A bed system comprising:
a bed; and
the biological state monitoring system as defined in claim 4.

* * * * *